United States Patent
Sanford et al.

(10) Patent No.: US 8,210,032 B2
(45) Date of Patent: *Jul. 3, 2012

(54) WATER DETECTION ARRANGEMENT

(75) Inventors: Emery Sanford, San Francisco, CA (US); Stephen P. Zadesky, Portola Valley, CA (US); Phillip M. Hobson, Menlo Park, CA (US); M. Evans Hankey, San Francisco, CA (US); Stephen Brian Lynch, Portola Valley, CA (US); Tang Yew Tan, Palo Alto, CA (US); Erik L. Wang, Redwood City, CA (US)

(73) Assignee: Apple Inc., Cupertino, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 12/688,817

(22) Filed: Jan. 15, 2010

(65) Prior Publication Data

US 2010/0117841 A1     May 13, 2010

Related U.S. Application Data

(63) Continuation of application No. 11/636,152, filed on Dec. 7, 2006, now Pat. No. 7,658,095.

(51) Int. Cl.
    *G01N 5/02* (2006.01)
(52) U.S. Cl. .......................................... 73/73; 73/29.02
(58) Field of Classification Search .................. None
    See application file for complete search history.

(56) References Cited

U.S. PATENT DOCUMENTS

| | | | |
|---|---|---|---|
| 4,058,632 A | 11/1977 | Evans | |
| 6,078,792 A | 6/2000 | Phillips | |
| 6,628,785 B1 * | 9/2003 | Kitamura et al. | 379/437 |
| 7,105,225 B2 | 9/2006 | Birkholz et al. | |
| 2005/0118415 A1 | 6/2005 | LaBrosse et al. | |
| 2006/0263597 A1 | 11/2006 | Birkholz et al. | |
| 2008/0134768 A1 | 6/2008 | Sanford | |
| 2009/0273480 A1 | 11/2009 | Mittleman et al. | |

FOREIGN PATENT DOCUMENTS

| | | |
|---|---|---|
| EP | 1001264 | 5/2000 |
| JP | 06248207 | 9/1994 |
| WO | 98/23920 | 6/1998 |
| WO | 03/015060 | 2/2003 |
| WO | 03/031531 | 4/2003 |

OTHER PUBLICATIONS

"3M Water Contact Indicator Tapes", Electronic Manuals, Mar. 2005.
Erik L. Wang, U.S. Appl. No. 12/472,192, filed May 26, 2009.

* cited by examiner

*Primary Examiner* — Hezron E Williams
*Assistant Examiner* — Mark A Shabman
(74) *Attorney, Agent, or Firm* — David C. Kellogg

(57) ABSTRACT

An electronic device having an enclosure is disclosed. The electronic device includes a hole disposed at least partially through the enclosure. The electronic device also includes a detector configured to provide at least one visual indication after being immersed in water. The detector may include a moisture-indicating portion and a light-permitting moisture-proof membrane. The detector may be disposed inside at least one of the enclosure and the hole such that at least a portion of the detector is visible through the hole from outside of the enclosure without dismantling or opening the electronic device. The distance between the light-permitting moisture-proof membrane and an opening of the hole in the enclosure may be less than the distance between the moisture-indicating portion and the opening of the hole.

20 Claims, 7 Drawing Sheets

WATER DETECTION ARRANGEMENT

This application is a continuation of patent application Ser. No. 11/636,152, filed Dec. 7, 2006, which is hereby incorporated by referenced herein in its entirety.

BACKGROUND

Water exposure is among major reasons that may cause significant malfunction of devices, such as electronic devices, which include electronic, mechanical, or chemical components. Therefore, verification of significant water exposure (or water immersion) is important to manufacturers of the devices. For example, for purposes such as warranty claim assessment, trouble-shooting for repairs, and product development, a manufacturer of electronic devices typically needs to verify whether a malfunctioning device has been immersed in water. FIGS. 1A-B illustrate an example conventional arrangement for verifying water immersion of a device 100 such as a cellular phone.

As illustrated in FIGS. 1A-B, device 100 includes a compartment 105 with a cover 108 for housing a removable module 110 such as a battery. For verifying water immersion, device 100 may include a detector 102 disposed at a bottom of compartment 105. To determine whether device 100 has previously been immersed in water, an inspector 170, such as a representative of the manufacture of device 100, may open cover 108 and remove removable module 110 to see whether detector 102 has changed color.

Detector 102 may be commercially available from suppliers such as 3M Company (www.3m.com) of St. Paul, Minn. and Schreiner Label Tech, Inc. of Southfield, Mich., and NovaVision Inc. (www.novavisioninc.com) of Bowling Green, Ohio and typically has a configuration as illustrated in FIG. 1B.

FIG. 1B illustrates a cross-sectional view of detector 102, with dimensions of detector 102 exaggerated for clear illustration. As shown in FIG. 1B, detector 102 includes an adhesive layer 132 for securing detector 102 at the bottom of compartment 105. Over adhesive layer 132, detector 102 includes a dye layer 112 that may dissolve after receiving a certain amount of water. Over dye layer 112, detector 102 includes a paper layer 122 for bearing dye layer 112 as well as allowing dissolved dye layer 112 to diffuse (or permeate) through paper layer 122 to show an indication (such as a red spot) that is visible to inspector 170 after detector 102 has been significantly exposed to (or immersed in) water. Over paper layer 122, detector 102 includes a transparent cover layer 142 for limiting exposure of paper layer 122 to humidity, thereby further avoiding false positives.

Nevertheless, the above-described conventional arrangement for verifying water immersion with detector 102 has disadvantages. The disadvantages may pertain to limited application, tampering of detection 102, and complicated inspection process, described as follows.

Firstly, application of the conventional arrangement is limited to devices that are designed to be easily opened. However, subject to requirements such as industrial standards, design considerations, or manufacturing considerations, some devices cannot be opened without being dismantled or damaged. Therefore, water immersion of some devices cannot be verified using the conventional arrangement.

Secondly, since detector 102 is readily visible and accessible with easy removal of removable module 110, detector 102 may be easily tampered. For example, detector 102 may be replaced with a new detector after device 100 has been immersed in water. As a result, it may become difficult for the manufacturer of device 100 to verify or prove water immersion of device 100.

Thirdly, the process of water immersion verification may be complicated. When the representative of the manufacturer is to inspect detector 120, the representative must remove cover 108 and removable module 110 before inspection. The representative may also need to make sure that cover 108 and removable module 110 are replaced back to device 100 after the inspection. Accordingly, the inspection process is complicated, and the inspection process may be further complicated when the representative handles multiple devices.

SUMMARY

These and other features of the present invention will be described in more detail below in the detailed description of the invention and in conjunction with the following figures.

One or more embodiments of the present invention involve an electronic device having an enclosure. The electronic device includes a hole disposed at least partially through the enclosure. The electronic device also includes a detector configured to provide at least one visual indication after being immersed in water. The detector may include a moisture-indicating portion and a light-permitting moisture-proof membrane. The detector may be disposed inside at least one of the enclosure and the hole such that at least a portion of the detector is visible through the hole from outside of the enclosure without dismantling or opening the electronic device. The distance between the light-permitting moisture-proof membrane and an opening of the hole in the enclosure may be less than the distance between the moisture-indicating portion and the opening of the hole.

One or more embodiments of the present invention involve a detector for verifying that a device has been significantly exposed to (or immersed in) water. The detector includes a first means for providing a visual proof for the verifying. The detector further includes a second means for securing the first means inside the device such that the visual proof is visible from outside of the device through a hole of the device without opening or dismantling the device.

One or more embodiments of the present invention involve a detector for providing at least one visual indication after the detector being immersed in water. The detector may include a moisture-indicating portion. The moisture-indicating portion may include a water-reactive element configured to perform a visible transformation after the moisture-indicating portion being immersed in the water. The at least one visual indication may include at least a portion of the visible transformation and may be shown on an observable side of the moisture-indicating portion. The detector may also include an adhesive disposed on the observable side of the moisture-indicating portion. The adhesive may be configured to secure the moisture-indicating portion inside an enclosure such that the at least one visual indication is visible from outside of the enclosure through a hole of the enclosure without opening or dismantling the enclosure.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1A:
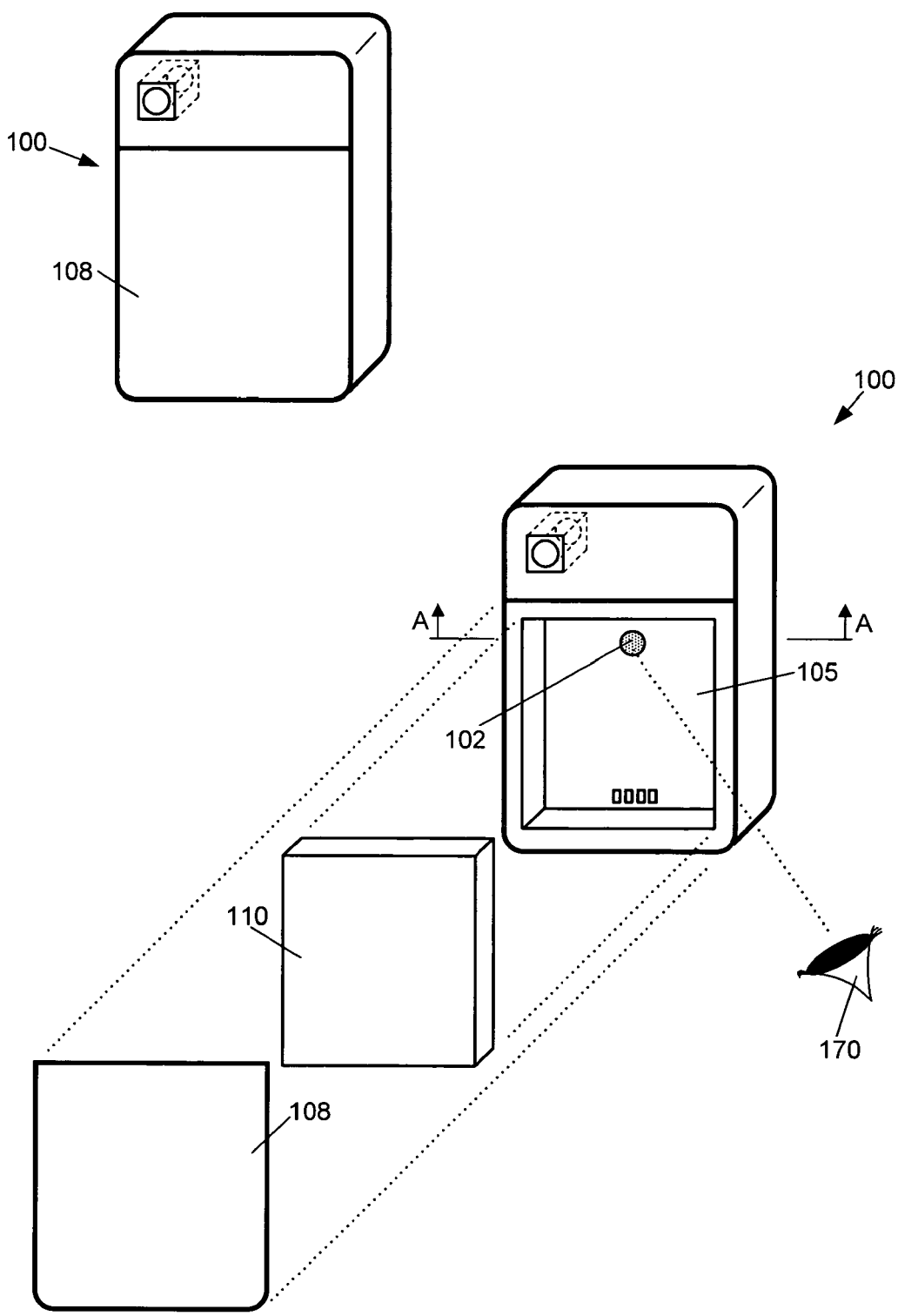
FIGS. 1A-B illustrate an example conventional arrangement for verifying water immersion of devices and an example conventional detector.

The present invention will now be described in detail with reference to a few embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

One or more embodiments of the present invention involve an electronic device with a detector for verifying water immersion of the electronic device without opening or dismantling the electronic device. The detector is configured to provide a visual indication if the detector has been immersed in water. In one or more embodiments, the electronic device includes a through hole that is disposed through an enclosure of the device, and the detector is disposed inside the enclosure such that the visual indication may be visible through the through hole from outside of the enclosure. In one or more embodiments, the electronic device includes a partially-through hole that is disposed partially through the enclosure, and the detector is disposed inside the partially-through hole such that the visual indication may be visible through the partially-through hole from outside of the enclosure.

In one or more embodiments, the through hole or the partially-through hole represents a hole of a connector that is fitted in an opening of the enclosure. The connector may be configured to provide electrical or mechanical coupling to a portion of a peripheral device. The portion of the peripheral device may be adapted to be inserted into the hole of the connector. For example, the connector may represent an audio jack connector for coupling to an audio headset.

Further, one or more embodiments of the present invention involve a detector for verifying water exposure or immersion of a device. The detector includes a moisture-indication portion for providing a visual proof for the verifying. The moisture-indication portion may include a water-reactive element, such as a dye, for performing a visible transformation after receiving a threshold amount of water. The visible transformation may include dissolution and then diffusion of the dye through an absorbent layer to expose the color of the dye. Alternatively or additionally, the visible transformation may include a color or pattern change of the moisture-indication portion. The detector may further include a means, such as an adhesive, for securing the moisture-indication portion inside the device such that the visual proof may be visible from outside of the device through a hole of the device without opening or dismantling the device.

The features and advantages of the present invention may be better understood with reference to the figures and discussions that follow.

Figure 2A:
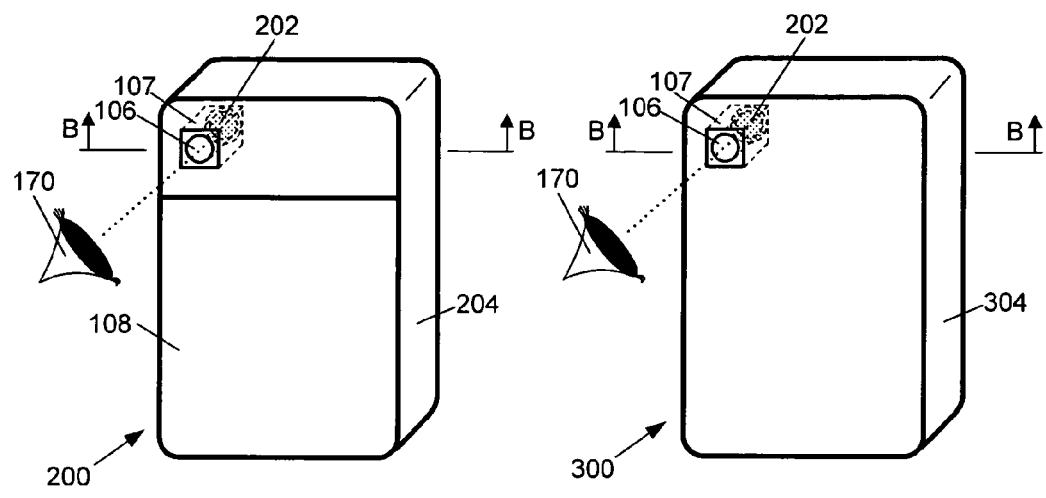
FIG. 2A illustrates, in accordance with one or more embodiments of the present invention, devices with a detector for verifying water immersion of the devices without opening or dismantling the devices.
Figure 2A:
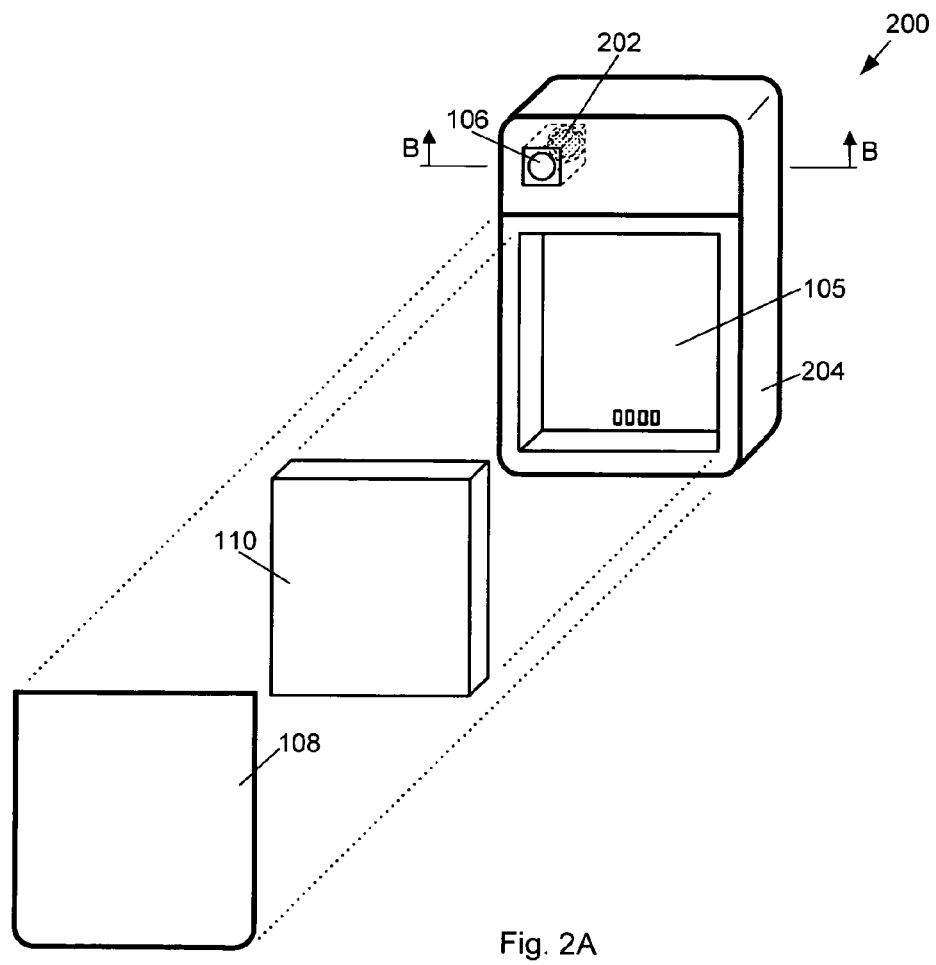

FIG. 2A illustrates, in accordance with one or more embodiments of the present invention, devices 200 and 300 with a detector 202 for verifying water immersion of devices 200 and 300 without opening or dismantling devices 200 and 300.

Figure 1B:
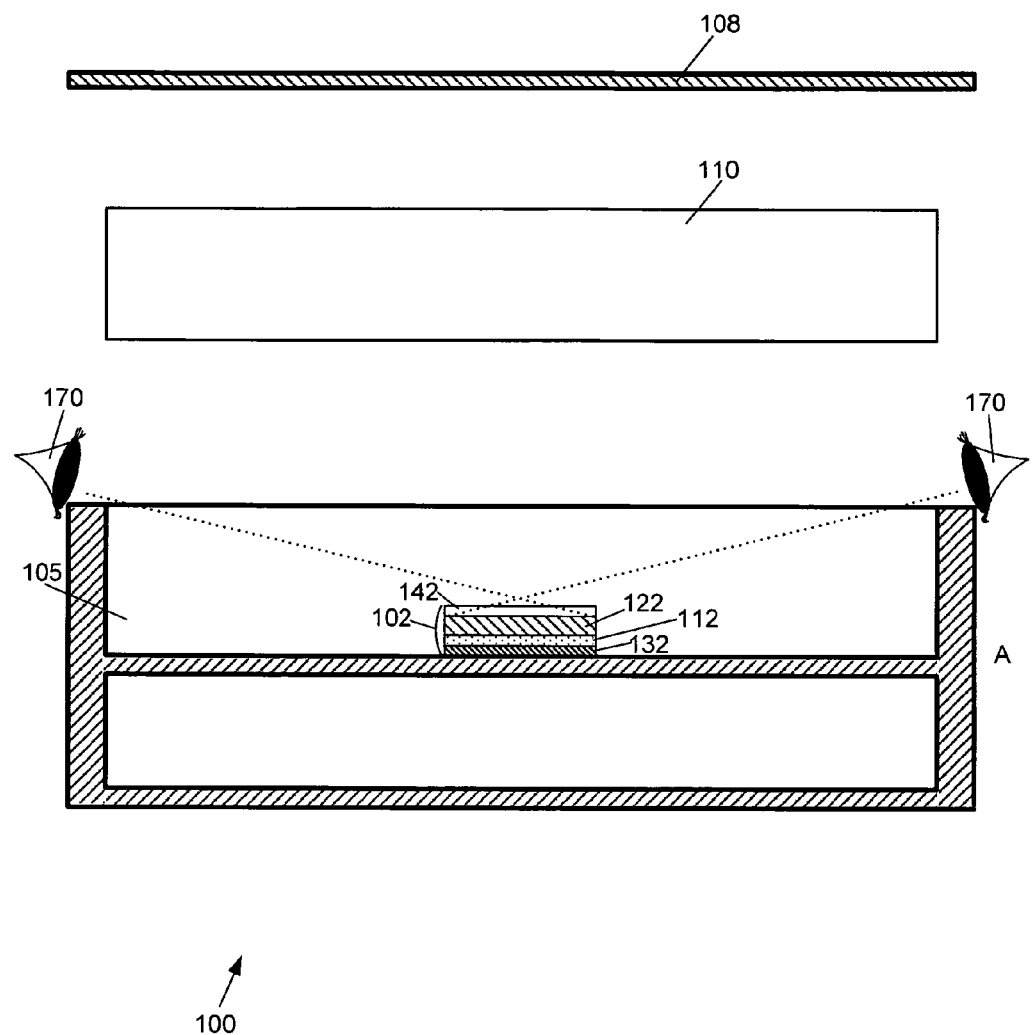

In one or more embodiments, device 200 includes enclosure 204, removable module 110, compartment 105 for housing removable module 110, and cover 108 for closing compartment 105, similar to device 100 (shown in the example of FIG. 1). However, device 200 does not include a detector in compartment 105. In a novel and non-obvious way, device 200 includes a detector 202 that is disposed inside enclosure 204. As shown in the example of FIG. 2A, device 200 includes a hole 106 that is disposed through enclosure 204, and detector 202 is disposed such that at least a portion of detector 202 is visible to inspector 170 through hole 106 from outside of enclosure 204. As such, detector 202 may be inspected without opening cover 108, and verifying water immersion of device 200 may be advantageously simpler than verifying water immersion of device 100.

Further, because detector 202 is disposed inside enclosure 204, detector 202 may not be tampered, damaged, or removed without enclosure 204 being evidently dismantled or damaged. Therefore, tampering, damage, removal, and loss of detector 202 may be advantageously avoided with one or more embodiments of the present invention.

In one or more embodiments, device 300 does not include a removable part or a compartment that can be easily opened by the consumer. In an arrangement similar to device 200, device 300 includes detector 202 disposed inside enclosure 304 such that detector 202 is visible to inspector 170 through hole 106, which is disposed through enclosure 304. As such, detector 202 may be inspected and water immersion of device 300 may be verified without dismantling or damaging enclosure 304 or device 300.

Hole 106 may represent a hole of a connector 107 that is fitted in an opening of enclosure 204 or 304. Connector 107 may be configured to provide electrical or mechanical coupling to a portion of a peripheral device for device 200 or 300, with the portion of the peripheral device adapted to be inserted into hole 106.

Figure 2B:
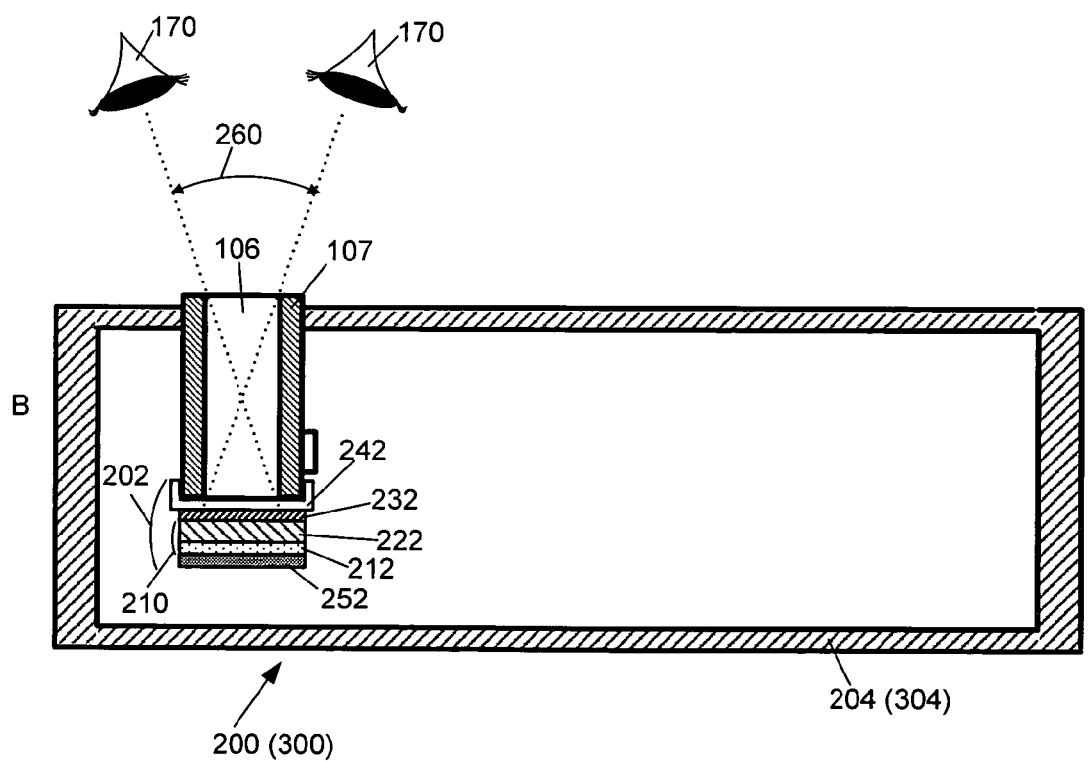
FIG. 2B illustrates, in accordance with one or more embodiments of the present invention, the detector in the example of FIG. 2A disposed inside an enclosure of one of the devices in the example of FIG. 2A.

FIG. 2B illustrates, in accordance with one or more embodiments of the present invention, detector 202 disposed inside enclosure 204 (304) of device 200 (300). Dimensions of components of detector 202 are exaggerated for clear illustration.

In one or more embodiments, detector 202 includes a moisture-indicating portion 210 configured to provide at least one visual indication after moisture-indicating portion 210 has been immersed in water. The at least one visual indication may include one or more of changing a color, changing a pattern, changing a dimension, changing a symbol, presenting a color, presenting a pattern, and presenting a symbol. In one or more embodiments, moisture-indicating 210 may include a water-reactive element 212 configured to perform a visible transformation after receiving a threshold amount of water. For example, water-reactive element 212 may include a dye that changes color or dissolves into a solution after receiving a threshold amount of water.

Moisture-indicating portion 210 may further include an absorbent 222 in contact with water-reactive element 212. For example, absorbent 222 may include a layer of paper, and water-reactive element 212 may be spread or deposited on absorbent 222 or attached to absorbent 222. In one or more embodiments, absorbent 222 may be configured to filter out humidity such that water-reactive element 212 may not provide false positives, i.e., perform the visible transformation without being immersed in water. In one or more embodiments, when moisture-indicating portion 210 is immersed in water, at least a portion of water-reactive element 212 may dissolve into a water solution, and the water solution may permeate through absorbent 222 to an observable side of absorbent 222 to provide the at least one visual indication. In the example of FIG. 2B, the observable side of absorbent 222 represents an upper side of absorbent 222 that is visible through 106 from outside of enclosure 204 (304).

In one or more embodiments, detector 202 includes a light-permitting membrane 242 configured to provide protection to moisture-indicating portion 210 while allowing moisture-indicating portion 202 to be visible through hole 106 from outside of enclosure 204 (304). In one or more embodiments, light-permitting membrane 242 is transparent. As shown in the example of FIG. 2B, light-permitting membrane 242 may be disposed over the observable side of absorbent 222 of moisture-indicating portion 210. As a result, moisture-indicating portion 210 may be protected from objects that come through hole 106.

Light-permitting membrane 242 may be made of moisture-proof material such as, for example, moisture-proof plastic. Accordingly, light-permitting membrane 242 may prevent water and humidity from permeating moisture-indicating portion 210 and from entering enclosure 204 (304) through hole 106. In the example of FIG. 2B, with a substantial surface covered by light-permitting membrane 242, moisture-indicating portion 210 may be prevented from providing false positives, i.e., providing the at least one visual indication without being immersed in water. Further, components of device 200 (300) inside enclosure 204 (304) may be protected from humidity and water that come into hole 106.

In one or more embodiments, detector 202 includes an adhesive 232 for securing moisture-indicating portion 210 inside enclosure 204 (304). In the example of FIG. 2B, adhesive 232 is disposed on the observable side of absorbent 222, and moisture-indicating portion 210 is attached to light-permitting membrane 242 by adhesive 232. In turn, light-permitting membrane is secured on a portion of connector 107 that is fitted in an opening of enclosure 204 (304).

Detector 202 may further include a cover 252 for shielding components inside enclosure 204 (304) from contacting moisture-indicating portion 210. Cover 252 may be made of non-conductive and/or moisture-proof material such that electrical circuitry in contact with detector 202 at cover 252 may not be affected by moisture-indicating portion 210.

Detector 202 may be readily custom-made by suppliers such as 3M Company (www.3m.com) of St. Paul, Minn.

As shown in the example of FIG. 2B, detector 202 may be visible to inspector 170 within only a small range, represented by viewing angle 260, such that a user of device 200 (300) may not notice the existence of detector 202, and therefore intention of the user to tamper detector 202 may be prevented.

Figure 3:
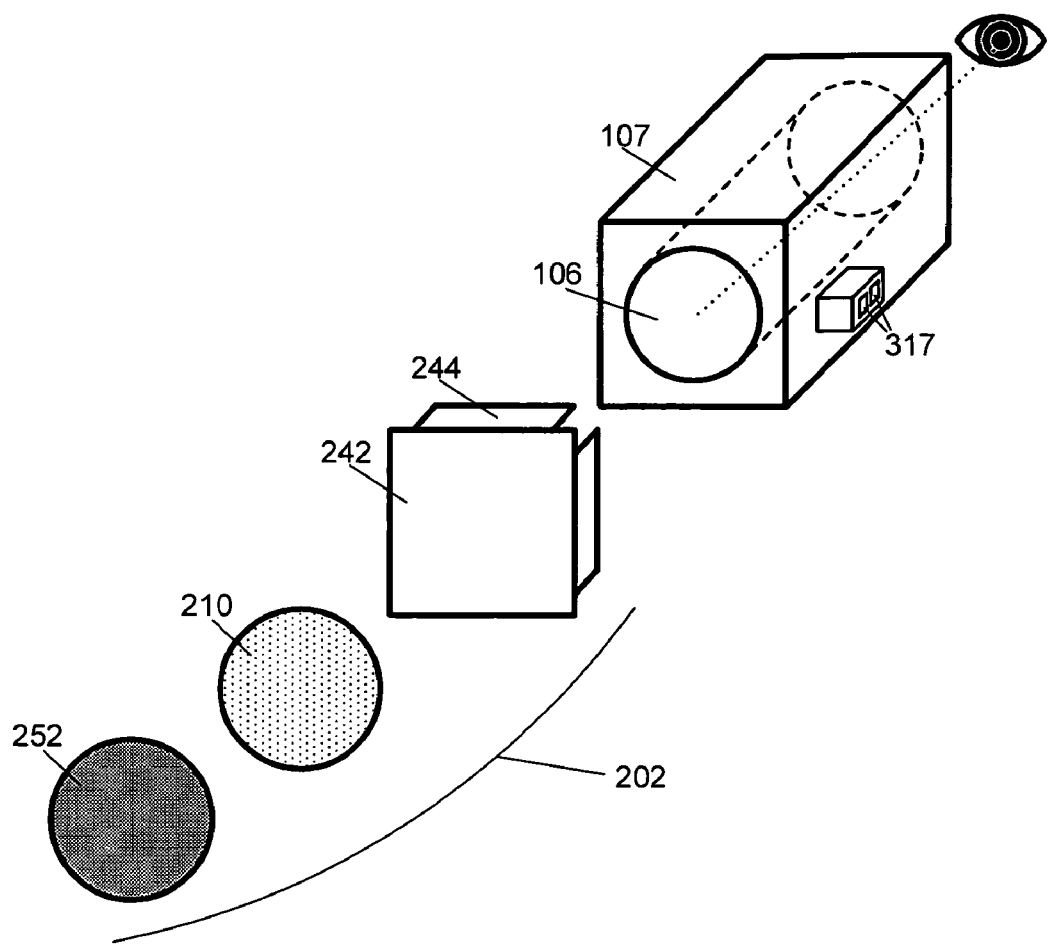
FIG. 3 illustrates, in accordance with one or more embodiments of the present invention, the detector in the example of FIG. 2A secured on a connector.
Figure 3:
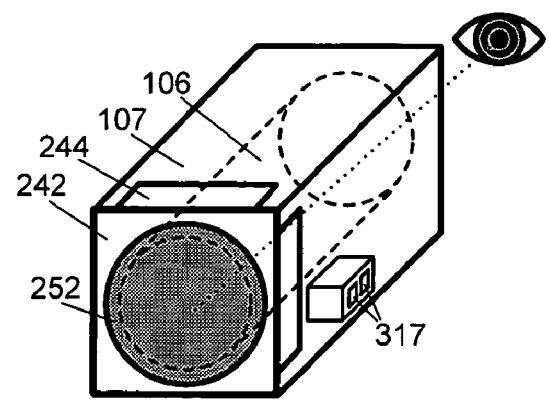

FIG. 3 illustrates, in accordance with one or more embodiments of the present invention, detector 202 secured on connector 107. As shown in the example of FIG. 3, light-permitting membrane 242 includes a flap 244 for facilitating light-permitting membrane to be secured on a portion of connector 107 through friction or an adhesive. Moisture-indicating portion 210 is secured on light-permitting membrane 242 such that at least a portion of moisture-indicating portion 210 is visible through hole 106. Further, moisture-indicating portion 210 is covered by cover 252.

As further illustrated in the example of FIG. 3, connector 107 includes conductive contacts 317 for transmitting one or more of audio signals, video signals, data, and electricity. Connector 107 may represent, for example, an audio jack connector.

Figure 4A:
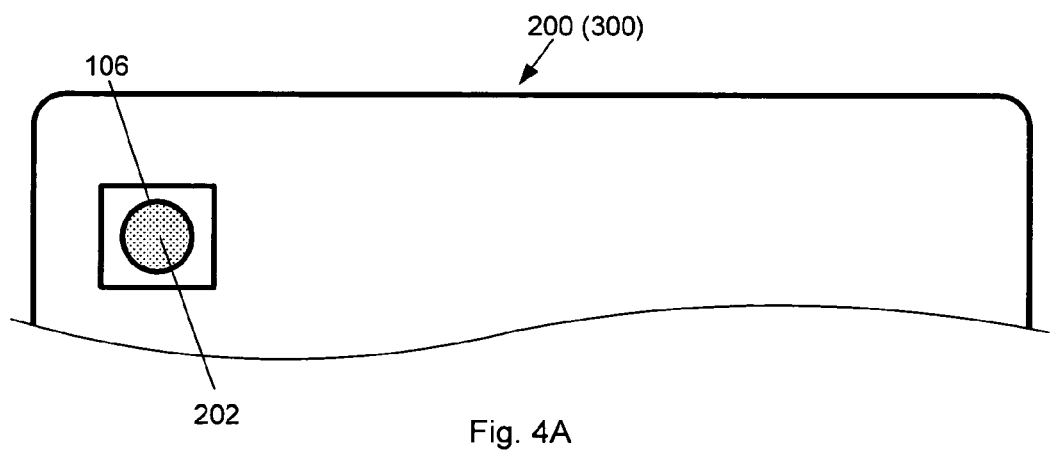
FIGS. 4A-B illustrate, in accordance with one or more embodiments of the present invention, the detector in the example of FIG. 2A before and after water immersion of one of the devices in the example of FIG. 2A.
Figure 4B:
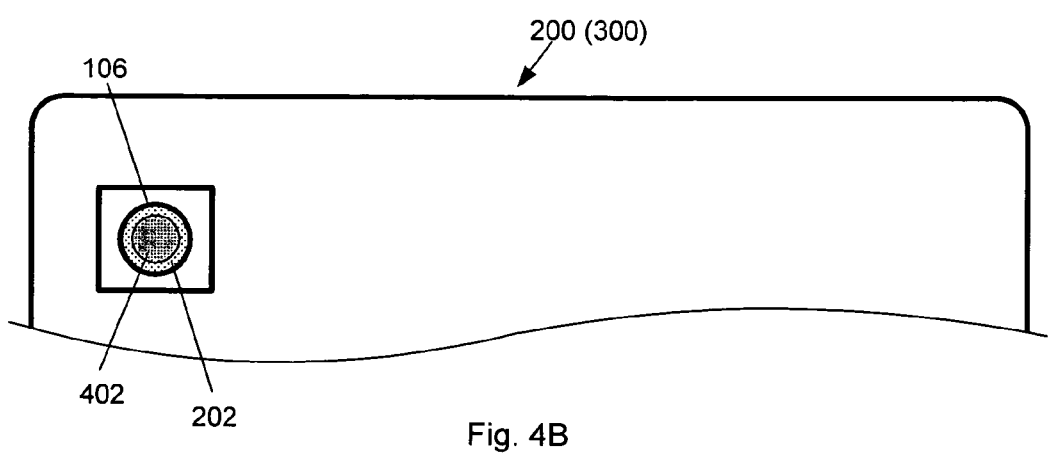

FIGS. 4A-B illustrate, in accordance with one or more embodiments of the present invention, detector 202 before and after water immersion of device 200 (300). As shown in the example of FIG. 4A, at least a portion of detector 202 is visible through hole 106 and provides no visual indication of water immersion before device 200 (300) is immersed in water. Contrarily, as shown in the example of FIG. 4B, after device 200 (300) has been immersed in water, detector 202 provides a visual indication 402 that is visible through hole 106. Visual indication 402 may represent a colored spot.

Figure 5:
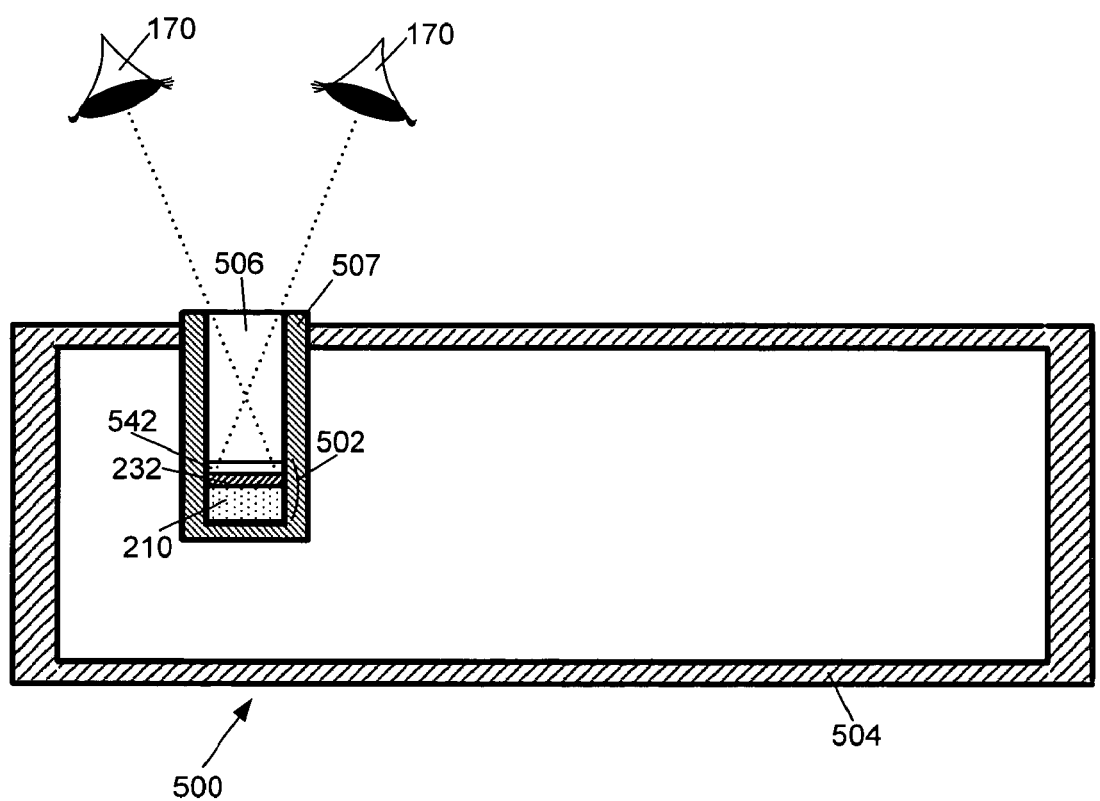
FIG. 5 illustrates, in accordance with one or more embodiments of the present invention, a detector disposed inside a hole of a device.

FIG. 5 illustrates, in accordance with one or more embodiments of the present invention, a detector 502 disposed inside a hole 506 of a device 500. As shown in the example of FIG. 5, detector 502 is visible to inspector 170 through hole 506 from outside of an enclosure 504 of device 500 such that inspector 170 is able to inspect detector 502 without opening or dismantling device 500.

As shown in the example of FIG. 5, hole 506 may represent a hole of a component 507. Component 507 is fitted in an opening of enclosure and may be considered part of enclosure 504. In one or more embodiments, hole 506 does not completely go through component 507 and is therefore only partially through enclosure 504. Component 507 may represent a connector configured to provide mechanical or electrical coupling to a peripheral device for device 500. Alternatively or additionally, hole 506 may represent a portion of a feature of enclosure 504.

In one or more embodiments, detector 502 includes a moisture-indicating portion 210 configured to provide at least one visual indication after moisture-indicating portion 210 has been immersed in water. Detector 502 may further include a light-permitting moisture-proof membrane 542 disposed over moisture-indicating portion 210 for preventing false positives, i.e., the at least on visual indication provided by moisture-indicating portion 210 without device 500 being immersed in water. Detector 502 may further include an adhesive 232 disposed between moisture-indicating portion 210 and light-permitting moisture-proof membrane 542 for joining moisture-indicating portion 210 and light-permitting moisture-proof membrane 542.

Moisture-indicating portion 210 may be secured inside hole 506 by one or more of an adhesive disposed at the bottom of hole 506, friction provided by an inside wall of component 507, and a constraint provided by light-permitting moisture-proof membrane 542. light-permitting moisture-proof membrane 542 may be secured inside hole 506 by at least one of adhesive 232 and friction provided by an inside wall of component 507.

Detector 502 may be readily custom-made by suppliers such as 3M Company (www.3m.com) of St. Paul, Minn.

As can be appreciated from the forgoing, embodiments of the present invention may advantageously enable verifying water immersion of a wide variety of devices without opening or dismantling the devices. As a result, processes of inspecting the devices for verifying water immersion may be significantly simplified. Further, with detectors disposed inside the devices, tampering of the detectors may be prevented.

While this invention has been described in terms of several embodiments, there are alterations, permutations, and equivalents, which fall within the scope of this invention. For example, although holes with circular openings are illustrated in the figures, holes with other configurations may also be employed in embodiments of the present invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. An electronic device comprising:
a housing;
a peripheral connector mounted within the housing, wherein the peripheral connector has an opening; and
a moisture-indicating detector viewable through the opening in the peripheral connector, wherein the electronic device is operable to communicate with external circuitry through the peripheral connector.

2. The electronic device defined in claim 1 further comprising:
electrical circuitry within the housing; and
conductive contacts within the peripheral connector.

3. The electronic device defined in claim 1 further comprising:
electrical circuitry within the housing; and
conductive contacts within the peripheral connector, wherein the conductive contacts provide at least one of audio signals, video signals, data, and electricity to the peripheral connector.

4. The electronic device defined in claim 1 wherein the moisture-indicating detector comprises:
a moisture-indicating portion;
a light-permitting membrane between the moisture-indicating portion and the peripheral connector; and
adhesive between the moisture-indicating portion and the light-permitting membrane.

5. The electronic device defined in claim 4 wherein the light-permitting membrane comprises:
a planar surface; and
at least one flap that is perpendicular to the planar surface and that is attached to the peripheral connector.

6. The electronic device defined in claim 1 wherein the moisture-indicating detector comprises:
a light-permitting membrane;
a moisture-indicating portion between the light-permitting membrane and the peripheral connector; and
adhesive between the moisture-indicating portion and the light-permitting membrane.

7. The electronic device defined in claim 1 wherein the moisture-indicating detector comprises:
a water-reactive element that includes a soluble dye;
an absorbent element that absorbs the soluble dye when the moisture-indicating detector is exposed to at least a given amount of water; and
a light-permitting moisture-proof membrane between the absorbent element and the opening in the peripheral connector.

8. The electronic device defined in claim 1 wherein the peripheral connector comprises an audio jack connector.

9. An electronic device that receives a removable peripheral component, the electronic device comprising:
a housing having a housing opening;
a connector in the housing, wherein the connector has an interior volume and has a connector opening to the interior volume, wherein the housing opening and the connector opening are aligned, and wherein the connector opening is configured to receive at least a portion of the removable peripheral component into the interior volume through the connector opening; and
a moisture-indicating detector viewable through the connector opening and the housing opening.

10. The electronic device defined in claim 9 wherein the connector comprises an audio jack connector.

11. The electronic device defined in claim 9 wherein the moisture-indicating detector comprises:
a moisture-indicating portion;
a light-permitting membrane between the moisture-indicating portion and the peripheral connector; and
adhesive between the moisture-indicating portion and the light-permitting membrane.

12. The electronic device defined in claim 11 wherein the light-permitting membrane comprises:
a planar surface; and
at least one flap that is perpendicular to the planar surface, wherein the electronic device further comprises:
adhesive that attaches the flap to the peripheral connector.

13. The electronic device defined in claim 9 wherein the moisture-indicating detector comprises:
a light-permitting membrane;
a moisture-indicating portion between the light-permitting membrane and the peripheral connector; and
adhesive between the moisture-indicating portion and the light-permitting membrane.

14. The electronic device defined in claim 9 wherein the moisture-indicating detector comprises:
a water-reactive element that includes a soluble dye;
an absorbent element that absorbs the soluble dye when the moisture-indicating detector is exposed to at least a given amount of water; and
a light-permitting moisture-proof membrane between the absorbent element and the opening in the peripheral connector.

15. An electronic device that receives a peripheral component, comprising:
a housing having an interior and an exterior;
a connector that has an interior volume, wherein the connector has a first connector opening between the interior volume and the exterior of the housing and has a second connector opening between the interior volume and the interior of the housing, wherein the connector is configured to receive at least a portion of the peripheral component into the interior volume through the first connector opening; and
a moisture-indicating detector that is attached to the connector covering the second opening and that is viewable through the first and second connector openings.

16. The electronic device defined in claim 15 wherein the connector comprises an audio jack connector.

17. The electronic device defined in claim 15 wherein the housing has a housing opening and wherein the housing opening is aligned with the first connector opening.

18. The electronic device defined in claim 17 wherein moisture-indicating detector comprises dye.

19. The electronic device defined in claim 15 wherein the moisture-indicating detector comprises:
a water-reactive element that includes a soluble dye; and
an absorbent element that absorbs the soluble dye when the moisture-indicating detector is exposed to at least a given amount of water.

20. The electronic device defined in claim 19 wherein the connector comprises an audio jack connector.

* * * * *